(12) United States Patent
Unger et al.

(10) Patent No.: US 9,345,536 B2
(45) Date of Patent: *May 24, 2016

(54) SURGICAL FORCEPS WITH BIFURCATED FLANGED JAW COMPONENTS

(71) Applicant: COVIDIEN LP, Mansfield, MA (US)

(72) Inventors: Jeffrey R. Unger, Longmont, CO (US); James D. Allen, IV, Broomfield, CO (US); Daniel A. Joseph, Golden, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/579,446

(22) Filed: Dec. 22, 2014

(65) Prior Publication Data
US 2015/0112338 A1 Apr. 23, 2015

Related U.S. Application Data

(63) Continuation of application No. 13/461,397, filed on May 1, 2012, now Pat. No. 8,920,461.

(51) Int. Cl.
A61B 18/14 (2006.01)
A61B 17/28 (2006.01)
A61B 17/285 (2006.01)
(Continued)

(52) U.S. Cl.
CPC ......... *A61B 18/1445* (2013.01); *A61B 17/2816* (2013.01); *A61B 18/1442* (2013.01); *A61B 17/285* (2013.01); *A61B 17/29* (2013.01); *A61B 2017/2947* (2013.01); *A61B 2018/0063* (2013.01); *A61B 2018/00607* (2013.01); *A61B 2018/1455* (2013.01)

(58) Field of Classification Search
None
See application file for complete search history.

(56) References Cited

U.S. PATENT DOCUMENTS

| 2,801,633 | A | 8/1957 | Ehrlich |
| 5,100,420 | A | 3/1992 | Green et al. |
| 5,242,456 | A | 9/1993 | Nash et al. |

(Continued)

FOREIGN PATENT DOCUMENTS

| CN | 100493469 | 6/2009 |
| CN | 101507635 | 8/2009 |

(Continued)

OTHER PUBLICATIONS

Int'l Search Report EP 04709033.7 dated Dec. 8, 2010.
(Continued)

*Primary Examiner* — Kennedy Schaetzle

(57) ABSTRACT

A forceps includes an end effector assembly having first and second jaw members. Each jaw member includes a bifurcated proximal flange extending therefrom defining first and second spaced-apart flange components. The first flange components are pivotably engaged to one another via a first engagement portion and the second flange components are pivotably engaged to one another via a second engagement portion. One or both of the jaw members is pivotable relative to the other about the first and second engagement portions between an open position and a closed position for grasping tissue therebetween. A guide member is configured for positioning between the proximal flanges of the jaw members. The guide member includes a tab extending transversely therefrom that is configured to operably engaged one of the first and second engagement portions to retain the jaw members in engagement with one another.

14 Claims, 7 Drawing Sheets

(51) Int. Cl.
    *A61B 17/29*        (2006.01)
    *A61B 18/00*        (2006.01)

(56) References Cited

U.S. PATENT DOCUMENTS

| | | | |
|---|---|---|---|
| 5,383,471 A | 1/1995 | Funnell | |
| 5,456,684 A | 10/1995 | Schmidt et al. | |
| 5,707,392 A | 1/1998 | Kortenbach | |
| H1745 H | 8/1998 | Paraschac | |
| 6,117,158 A | 9/2000 | Measamer et al. | |
| H1904 H | 10/2000 | Yates et al. | |
| H2037 H | 7/2002 | Yates et al. | |
| 6,733,514 B2 | 5/2004 | Miser | |
| 7,103,947 B2 | 9/2006 | Sartor et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al | |
| D545,432 S | 6/2007 | Watanabe | |
| D547,154 S | 7/2007 | Lee | |
| 7,244,257 B2 | 7/2007 | Podhajsky et al. | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| 7,431,730 B2 | 10/2008 | Viola | |
| D582,038 S | 12/2008 | Swoyer et al. | |
| 7,594,313 B2 | 9/2009 | Prakash et al. | |
| 7,641,653 B2 | 1/2010 | Dalla Betta et al. | |
| 7,722,607 B2 | 5/2010 | Dumbauld et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 7,896,878 B2 | 3/2011 | Johnson et al. | |
| D649,249 S | 11/2011 | Guerra | |
| D649,643 S | 11/2011 | Allen, IV et al. | |
| D661,394 S | 6/2012 | Romero et al. | |
| 8,246,618 B2 | 8/2012 | Bucciaglia et al. | |
| 8,328,802 B2 | 12/2012 | Deville et al. | |
| 8,920,461 B2 | 12/2014 | Unger et al. | |
| 8,926,610 B2 | 1/2015 | Hafner et al. | |
| 2002/0058925 A1 | 5/2002 | Kaplan et al. | |
| 2008/0015566 A1 | 1/2008 | Livneh | |
| 2009/0012520 A1 | 1/2009 | Hixson et al. | |
| 2009/0043304 A1 | 2/2009 | Tetzlaff et al. | |
| 2009/0043305 A1 | 2/2009 | Brodbeck et al. | |
| 2009/0088743 A1 | 4/2009 | Masuda | |
| 2009/0088750 A1 | 4/2009 | Hushka et al. | |
| 2009/0182327 A1 | 7/2009 | Unger | |
| 2011/0009864 A1 | 1/2011 | Bucciaglia et al. | |
| 2011/0071522 A1 | 3/2011 | Dumbauld et al. | |
| 2011/0251606 A1 | 10/2011 | Kerr | |
| 2011/0319888 A1 | 12/2011 | Mueller et al. | |
| 2012/0083786 A1 | 4/2012 | Artale et al. | |

FOREIGN PATENT DOCUMENTS

| | | |
|---|---|---|
| CN | 21299462 | 9/2009 |
| DE | 2415263 A1 | 10/1975 |
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | D4303882 C2 | 2/1995 |
| DE | D4403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 20 2007 009317 U1 | 8/2007 |
| DE | 202007009165 U1 | 8/2007 |
| DE | 202007009318 U1 | 8/2007 |
| DE | 10031773 B4 | 11/2007 |
| DE | 202007016233 U1 | 1/2008 |
| DE | 102006059175 A1 | 6/2008 |
| DE | 19738457 B4 | 1/2009 |
| DE | 102004026179 B4 | 1/2009 |
| DE | 102008018406 B3 | 7/2009 |
| EP | 0584787 A1 | 3/1994 |
| EP | 1 159 926 A2 | 12/2001 |
| EP | 1532932 A1 | 5/2005 |
| EP | 1609430 A1 | 12/2005 |
| EP | 1810625 | 7/2007 |
| EP | 1810625 A1 | 7/2007 |
| EP | 2347725 A1 | 7/2011 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 9-10223 C | 1/1997 |
| JP | 9-122138 A | 5/1997 |
| JP | 0010000195 A | 1/1998 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-253789 A | 9/2005 |
| JP | 2006-015078 A | 1/2006 |
| JP | 2006-501939 A | 1/2006 |
| JP | 2006-095316 A | 4/2006 |
| JP | 2011125195 A | 6/2011 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |

(56) References Cited

FOREIGN PATENT DOCUMENTS

| WO | 02/45589 | 6/2002 |
|---|---|---|
| WO | 2005/110264 A2 | 11/2005 |
| WO | 2010/014825 A1 | 2/2010 |

OTHER PUBLICATIONS

Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05004431.2 dated Jun. 2, 2005.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 0044292 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report Ep 07 016911.5 extended dated Mar. 2, 2011.
Int'l Search Report EP 07 020283.3 dated Feb. 5, 2008.
U.S. Appl. No. 08/926,869, James G. Chandler, filed Sep. 10, 1997.
U.S. Appl. No. 09/177,950, Randell A. Frazier, filed Oct. 23, 1998.
U.S. Appl. No. 09/387,883, Dale F. Schmaltz, filed Sep. 1, 1999.
Int'l Search Report EP 11 006233.8 dated Feb. 2, 2012.
Int'l Search Report EP 11 007972.0 dated Dec. 28, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 153503.5 dated Mar. 5, 2012.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report Ep 11 180182.5 dated Nov. 15, 2011.
Int'l Search Report EP 11 180183 dated Nov. 30, 2011.
Int'l Search Report EP 11 183265.5 dated Nov. 28, 2011.
Int'l Search Report EP 11 183476.8 dated Jan. 18, 2012.
Int'l Search Report EP 11 185028.5 dated Jan. 2, 2012.
Int'l Search Report EP 11 189521.5 dated Feb. 20, 2012.
Int'l Search Report EP 11 190723.4 dated Mar. 16, 2012.
Int'l Search Report EP 12 155726.8 dated May 25, 2012.
Int'l Search Report EP 12 155728.4 dated Jul. 4, 2012.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020528.9 dated Aug. 4, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 015215.8 dated Feb. 24, 2010.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.

(56) References Cited

OTHER PUBLICATIONS

Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175559.3 dated May 25, 2012.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019.9 dated Aug. 22, 2011.
Int'l Search Report EP 10 182022.3 dated Mar. 11, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties at VHF Through Microwave Frequencies", IEEE Transactions on Microwave Theory and Techniques, vol. TT-28, No. 4, Apr. 1980.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.

(56) References Cited

OTHER PUBLICATIONS

U.S. Appl. No. 13/277,926, David M. Garrison, filed Oct. 20, 2011.
U.S. Appl. No. 13/277,962, David M. Garrison, filed Oct. 20, 2011.
U.S. Appl. No. 13/293,754, Jeffrey M. Roy, filed Nov. 10, 2011.
U.S. Appl. No. 13/306,523, David M. Garrison, filed Nov. 29, 2011.
U.S. Appl. No. 13/306,553, Duane E. Kerr, filed Nov. 29, 2011.
U.S. Appl. No. 13/308,104, John R. Twomey , filed Nov. 30, 2011.
U.S. Appl. No. 13/312,172, Robert J. Behnke, II., filed Dec. 6, 2011.
U.S. Appl. No. 13/324,863, William H. Nau, Jr., filed Dec. 13, 2011.
U.S. Appl. No. 13/344,729, James D. Allen, IV., Jan. 6, 2012.
U.S. Appl. No. 13/355,829, John R.Twomey, filed Jan. 23, 2012.
U.S. Appl. No. 13/357,979, David M. Garrison, filed Jan. 25, 2012.
U.S. Appl. No. 13/358,136, James D. Allen, IV., filed Jan. 25, 2012.
U.S. Appl. No. 13/360,925, James H. Orszulak, filed Jan. 30, 2012.
U.S. Appl. No. 13/400,290, Eric R. Larson, filed Feb. 20, 2012.
U.S. Appl. No. 13/404,435, Kim V. Brandt, filed Feb. 24, 2012.
U.S. Appl. No. 13/404,476, Kim V. Brandt, filed Feb. 24, 2012.
U.S. Appl. No. 13/412,879, David M. Garrison, filed Mar. 6, 2012.
U.S. Appl. No. 13/412,897, Joanna Ackley, filed Mar. 6, 2012.
U.S. Appl. No. 13/421,373, John R. Twomey, filed Mar. 15, 2012.
U.S. Appl. No. 13/430,325, William H. Nau, Jr., filed Mar. 26, 2012.
U.S. Appl. No. 13/433,924, Keir Hart, filed Mar. 29, 2012.
U.S. Appl. No. 13/448,577, David M. Garrison, filed Apr. 17, 2012.
U.S. Appl. No. 13/460,455, Luke Waaler, filed Apr. 30, 2012.
U.S. Appl. No. 13/461,335, James D. Allen, IV, filed May 1, 2012.
U.S. Appl. No. 13/461,378, James D. Allen, IV, filed May 1, 2012.
U.S. Appl. No. 13/461,397, James R. Unger, filed May 1, 2012.
U.S. Appl. No. 13/461,410, James R. Twomey, May 1, 2012.
U.S. Appl. No. 13/464,569, Duane E. Kerr, filed May 4, 2012.
U.S. Appl. No. 13/466,274, Stephen M. Kendrick, filed May 8, 2012.
U.S. Appl. No. 13/467,767, Duane E. Kerr, filed May 9, 2012.
U.S. Appl. No. 13/470,543, Sean T. Dycus, filed May 14, 2012.
U.S. Appl. No. 13/470,775, James D. Allen, IV, filed May 14, 2012.
U.S. Appl. No. 13/470,797, John J. Kappus, filed May 14, 2012.
U.S. Appl. No. 13/482,589, Eric R. Larson, filed May 29, 2012.
U.S. Appl. No. 13/483,733, Dennis W Butcher, filed May 30, 2012.
U.S. Appl. No. 13/488,093, Kristin D. Johnson, filed Jun. 4, 2012.
U.S. Appl. No. 13/491,853, Jessica E. Olson, filed Jun. 8, 2012.
U.S. Appl. No. 13/537,517, David N. Heard, filed Jun. 29, 2012.
U.S. Appl. No. 13/537,577, Tony Moua, filed Jun. 29, 2012.
U.S. Appl. No. 13/550,322, John J. Kappus, filed Jul. 16, 2012.
U.S. Appl. No. 13/571,055, Paul Guerra, filed Aug. 9, 2012.
U.S. Appl. No. 13/571,821, Joseph D. Bucciaglia, filed Aug. 10, 2012.
U.S. Appl. No. 13/584,194, Sean T. Dycus, filed Aug. 13, 2012.
European Search Report from corresponding application No. EP 13 16 6210 dated Apr. 29, 2014.
European Search Report issued in corresponding application No. EP 15167291.2 on Jul. 29, 2015.
U.S. Appl. No. 09/591,328, Thomas P. Ryan, filed Jun. 9, 200.
U.S. Appl. No. 12/336,970, Paul R. Sremeich, filed Dec. 17, 2008.
U.S. Appl. No. 13/050,182, Glenn A. Homer, filed Mar. 17, 2011.
U.S. Appl. No. 13/072,945, Patrick L. Dumbauld, filed Mar. 28, 2011.
U.S. Appl. No. 13/080,383, David M. Garrison, filed Apr. 5, 2011.
U.S. Appl. No. 13/085,144, Keir Hart, filed Apr. 12, 2011.
U.S. Appl. No. 13/091,331, Jeffrey R. Townsend, filed Apr. 21, 2011.
U.S. Appl. No. 13/102,573, John R. Twomey, filed May 6, 2011.
U.S. Appl. No. 13/102,604, Paul E. Ourada, filed May 6, 2011.
U.S. Appl. No. 13/108,093, Boris Chernov, filed May 16, 2011.
U.S. Appl. No. 13/108,129, Boris Chernov, filed May 16, 2011.
U.S. Appl. No. 13/108,152, Boris Chernov, filed May 16, 2011.
U.S. Appl. No. 13/108,177, Boris Chernov, filed May 16, 2011.
U.S. Appl. No. 13/108,196, Boris Chernov, filed May 16, 2011.
U.S. Appl. No. 13/108,441, Boris Chernov, filed May 16, 2011.
U.S. Appl. No. 13/108,468, Boris Chernov, filed May 16, 2011.
U.S. Appl. No. 13/111,642, John R. Twomey, filed May 19, 2011.
U.S. Appl. No. 13/111,678, Nikolay Kharin, filed May 19, 2011.
U.S. Appl. No. 13/113,231, David M. Garrison, filed May 23, 2011.
U.S. Appl. No. 13/157,047, John R. Twomey, filed Jun. 9, 2011.
U.S. Appl. No. 13/162,814, Barbara R. Tyrrell, filed Jun. 17, 2011.
U.S. Appl. No. 13/166,477, Daniel A. Joseph, filed Jun. 22, 2011.
U.S. Appl. No. 13/166,497, Daniel A. Joseph, filed Jun. 22, 2011.
U.S. Appl. No. 13/179,919, Russell D. Hempstead, filed Jul. 11, 2011.
U.S. Appl. No. 13/179,960, Boris Chernov, filed Jul. 11, 2011.
U.S. Appl. No. 13/179,975, Grant T. Sims, filed Jul. 11, 2011.
U.S. Appl. No. 13/180,018, Chase Collings, filed Jul. 11, 2011.
U.S. Appl. No. 13/183,856, John R. Twomey, filed Jul. 15, 2011.
U.S. Appl. No. 13/185,593, James D. Allen, IV, filed Jul. 19, 2011.
U.S. Appl. No. 13/204,841, Edward J. Chojin, filed Aug. 8, 2011.
U.S. Appl. No. 13/205,999, Jeffrey R. Unger, filed Aug. 9, 2011.
U.S. Appl. No. 13/212,297, Allan J. Evans, filed Aug. 18, 2011.
U.S. Appl. No. 13/212,308, Allan J. Evans, filed Aug. 18, 2011.
U.S. Appl. No. 13/212,329, Allan J. Evans, filed Aug. 18, 2011.
U.S. Appl. No. 13/212,343, Duane E. Kerr, filed Aug. 18, 2011.
U.S. Appl. No. 13/223,521, John R. Twomey, filed Sep. 1, 2011.
U.S. Appl. No. 13/227,220, James D. Allen, IV, filed Sep. 7, 2011.
U.S. Appl. No. 13/228,742, Duane E. Kerr, filed Sep. 9, 2011.
U.S. Appl. No. 13/231,643, Keir Hart, filed Sep. 13, 2011.
U.S. Appl. No. 13/234,357, James D. Allen, IV, filed Sep. 16, 2011.
U.S. Appl. No. 13/236,168, James D. Allen, IV, filed Sep. 19, 2011.
U.S. Appl. No. 13/236,271, Monte S. Fry, filed Sep. 19, 2011.
U.S. Appl. No. 13/243,628, William Ross Whitney, filed Sep. 23, 2011.
U.S. Appl. No. 13/247,778, John R. Twomey, filed Sep. 28, 2011.
U.S. Appl. No. 13/247,795, John R. Twomey, filed Sep. 28, 2011.
U.S. Appl. No. 13/248,976, James D. Allen, IV, filed Sep. 29, 2011.
U.S. Appl. No. 13/249,013, Jeffrey R. Unger, filed Sep. 29, 2011.
U.S. Appl. No. 13/249,024, John R. Twomey, filed Sep. 29, 2011.
U.S. Appl. No. 13/251,380, Duane E. Kerr, filed Oct. 3, 2011.
U.S. Appl. No. 13/277,373, Glenn A. Homer, filed Oct. 20, 2011.
European Search Report EP13757413 dated Sep. 14, 2015.
Chinese office action issued in corresponding application No. 201310154366.X on Feb. 1, 2016.

SURGICAL FORCEPS WITH BIFURCATED FLANGED JAW COMPONENTS

CROSS-REFERENCE TO RELATED APPLICATIONS

This application is a continuation application of U.S. patent application Ser. No. 13/461,397, filed on May 1, 2012, the entire contents of which are incorporated herein by reference.

BACKGROUND

1. Technical Field

The present disclosure relates to surgical instruments and, more particularly, to an open surgical forceps for grasping, sealing, and/or dividing tissue, and methods of manufacturing thereof.

2. Description of Related Art

A forceps is a plier-like instrument which relies on mechanical action between its jaws to grasp, clamp and constrict vessels or tissue. Electrosurgical forceps utilize both mechanical clamping action and electrical energy to affect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles.

Typically, once a vessel is sealed, the surgeon has to accurately sever the vessel along the newly formed tissue seal. Accordingly, many vessel sealing instruments have been designed which incorporate a knife or blade member which effectively severs the tissue after forming a tissue seal.

SUMMARY

As used herein, the term "distal" refers to the portion that is being described which is further from a user, while the term "proximal" refers to the portion that is being described which is closer to a user.

In accordance with one aspect of the present disclosure, a forceps is provided. The forceps includes an end effector assembly having first and second jaw members. Each of the jaw members includes a proximal flange extending therefrom. The proximal flange of each jaw member defines a bifurcated configuration having first and second spaced-apart flange components. The first flange components of the jaw members are configured to pivotably engage one another via a first engagement portion and the second flange components of the jaw members are configured to pivotably engage one another via a second engagement portion independent of the first engagement. One or both of the jaw members is pivotable relative to the other about the first and second engagement portions between an open position and a closed position for grasping tissue therebetween. A guide member configured for positioning between the proximal flanges of the first and second jaw members is also provided. The guide member includes one (or more) tabs extending transversely therefrom that is configured to operably engage one of the first and second engagement portions to retain the jaw members in engagement with one another.

In one aspect, the first flange component of each of the jaw members includes an aperture defined transversely therethrough. One of the first flange components also includes a boss disposed about the aperture thereof. The boss is configured for engagement within the aperture of the other first flange component for pivotably engaging the first flange components to one another. The second flange components may be similarly configured.

In another aspect, the tab is configured for engagement within the apertures defined through the first flange components (or the second flange components) of the jaw members. More specifically, the tab may be configured to resiliently bias into engagement within the apertures defined within the first flange components.

In another aspect, the proximal flanges of the jaw members are disposed in an overlapping, offset configuration relative to one another.

In still another aspect, the proximal flanges cooperate to define a lumen extending longitudinally therethrough. The guide member may be configured to substantially fill a volume of the lumen to inhibit lateral movement of the jaw members relative to one another.

In yet another aspect, the guide member is formed from first and second guide components, e.g., snap-fit in engagement with one another.

In still yet another aspect, the guide member defines a knife track extending longitudinally therethrough. The knife track is configured to guide reciprocation of a knife therethrough for cutting tissue grasped between the jaw members.

In another aspect, the guide member defines one or more wire guides extending longitudinally therethrough. The wire guide(s) is configured to route one or more wires therethrough for coupling to the first jaw member and/or the second jaw member to provide electrosurgical energy thereto.

In yet another aspect, first and second shaft members are coupled to the first and second jaw members, respectively. The shaft members are movable relative to one another between a spaced-apart position and an approximated position to move the jaw members between the open position and the closed position.

The first and second flange components of each of the jaw members may be welded to the respective shaft member thereof. Further, each jaw member may include a plurality of individual layer components joined together.

In accordance with another aspect of the present disclosure, a forceps is provided including first and second shaft members, each shaft member having a jaw member disposed at a distal end thereof. Each of the jaw members includes a proximal flange extending therefrom that defines a bifurcated configuration having first and second spaced-apart flange components. The first flange components of the jaw members are pivotably engaged to one another via a first engagement portion and the second flange components of the jaw members are pivotably engaged one another via a second engagement portion such that movement of the shaft members relative to one another between a spaced-apart position and an approximated position effects movement of the jaw members between an open position and a closed position for grasping tissue therebetween. The proximal flanges of the first and second jaw members cooperate to define a lumen extending longitudinally therethrough between the first and second engagement portions thereof. A guide member is disposed within the lumen and is engaged within one of the first and second engagement portions such that the proximal flanges are maintained in engagement with one another.

In one aspect, a knife assembly is disposed within one of the jaw members. The knife assembly includes a knife that is selectively translatable between a retracted position, wherein the knife is disposed within the jaw member, and an extended position, wherein the knife is advanced between the jaw members to cut tissue grasped therebetween. In such an aspect, the guide member may include a knife track defined therein that is configured to guide translation of the knife between the retracted and extended positions.

In another aspect, the jaw members each include an electrically-conductive tissue sealing plate disposed thereon in opposed relation relative to one another. One or both of the tissue sealing plates is adapted to connect to a source of electrosurgical energy for sealing tissue grasped between the jaw members. In such an aspect, the guide member may further be configured to define one or more wire guides extending longitudinally therethrough. The wire guide(s) is configured to route one or more wire therethrough for providing electrosurgical energy to the tissue sealing plates of the jaw members.

BRIEF DESCRIPTION OF THE DRAWINGS

Various aspects of the present disclosure are described herein with reference to the drawings wherein like reference numerals identify similar or identical elements.

DETAILED DESCRIPTION

Figure 1:
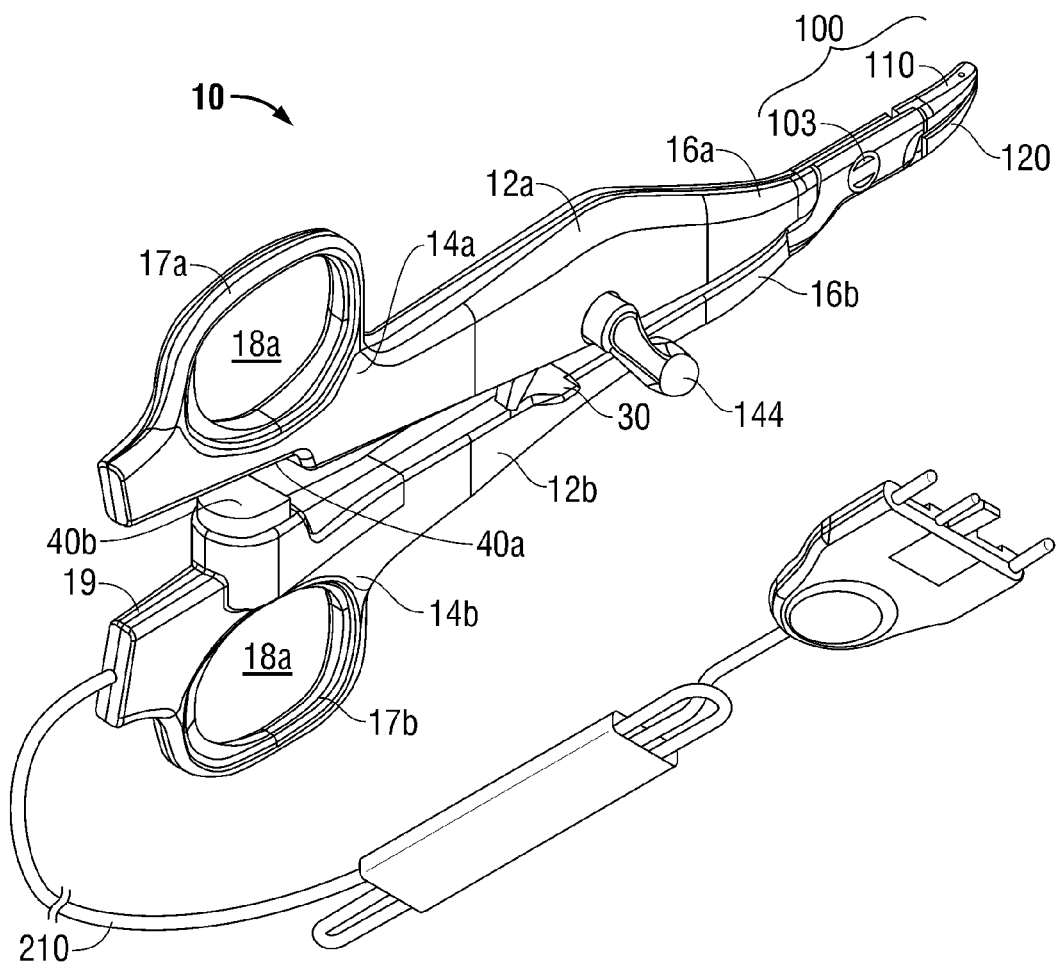
FIG. 1 is a side, perspective view of a forceps according to an aspect of the present disclosure.

Referring now to FIG. 1, an open forceps 10 contemplated for use in connection with traditional open surgical procedures is shown. For the purposes herein, either an open instrument, e.g., forceps 10, or an endoscopic instrument (not shown) may be utilized in accordance with the present disclosure. Obviously, different electrical and mechanical connections and considerations apply to each particular type of instrument; however, the novel aspects with respect to the end effector assembly and its operating characteristics remain generally consistent with respect to both the open and endoscopic configurations.

With continued reference to FIG. 1, forceps 10 includes two elongated shafts 12a and 12b, each having a proximal end 14a and 14b, and a distal end 16a and 16b, respectively. Forceps 10 further includes an end effector assembly 100 attached to distal ends 16a and 16b of shafts 12a and 12b, respectively. End effector assembly 100 includes a pair of opposing jaw members 110 and 120 that are pivotably connected about a pivot 103. Each shaft 12a and 12b includes a handle 17a and 17b disposed at the proximal end 14a and 14b thereof. Each handle 17a and 17b defines a finger hole 18a and 18b therethrough for receiving a finger of the user. As can be appreciated, finger holes 18a and 18b facilitate movement of the shaft members 12a and 12b relative to one another between a spaced-apart position and an approximated position, which, in turn, pivots jaw members 110 and 120 from an open position, wherein the jaw members 110 and 120 are disposed in spaced-apart relation relative to one another, to a closed position, wherein the jaw members 110 and 120 cooperate to grasp tissue therebetween.

A ratchet 30 may be included for selectively locking the jaw members 110 and 120 relative to one another at various positions during pivoting. Ratchet 30 may include graduations or other visual markings that enable the user to easily and quickly ascertain and control the amount of closure force desired between the jaw members 110 and 120.

Continuing with reference to FIG. 1, one of the shafts, e.g., shaft 12b, includes a proximal shaft connector 19 that is designed to connect the forceps 10 to a source of electrosurgical energy such as an electrosurgical generator (not shown). Proximal shaft connector 19 secures an electrosurgical cable 210 to forceps 10 such that the user may selectively apply electrosurgical energy to the electrically-conductive tissue sealing plates 112 and 122 (see FIGS. 3-4) of jaw members 110 and 120, respectively. More specifically, cable 210 includes a wire (or wires) (not shown) extending therethrough that has sufficient length to extend through one of the shaft members, e.g., shaft member 12b, in order to provide electrical energy to at least one of the sealing plates 112, 122 of jaw members 110, 120, respectively, of end effector assembly 100, e.g., upon activation of activation switch 40b. Alternatively, forceps 10 may be configured as a battery-powered instrument.

Activation switch 40b is disposed at proximal end 14b of shaft member 12b and extends from shaft member 12b toward shaft member 12a. A corresponding surface 40a is defined along shaft member 12a toward proximal end 14a thereof and is configured to actuate activation switch 40b. More specifically, upon approximation of shaft members 12a, 12b, e.g., when jaw members 110, 120 are moved to the closed position, activation switch 40b is moved into contact with, or in close proximity of surface 40a. Upon further approximation of shaft members 12a, 12b, e.g., upon application of a predetermined closure force to jaw members 110, 120, activation switch 40b is advanced further into surface 40a to depress activation switch 40b. Activation switch 40b controls the supply of electrosurgical energy to jaw members 110, 120 such that, upon depression of activation switch 40b, electrosurgical energy is supplied to sealing surface 112 and/or sealing surface 122 of jaw members 110, 120, respectively, to seal tissue grasped therebetween. Other more standardized activation switches are also contemplated, e.g., finger switch, toggle switch, foot switch, etc.

Figure 2A:
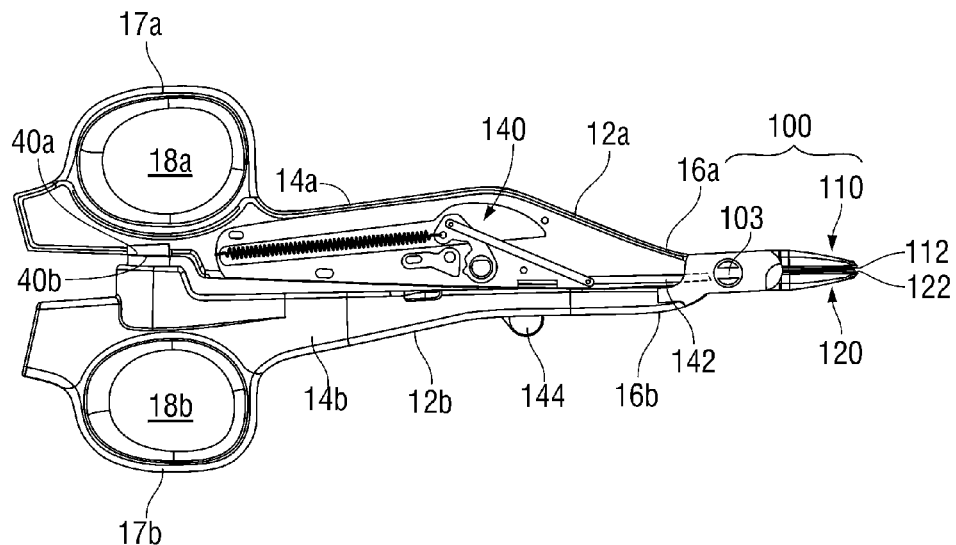
FIG. 2A is side view of the forceps of FIG. 1 wherein a portion of one of the shaft members has been removed to shown the internal components thereof and wherein a knife assembly of the forceps is disposed in a retracted position.
Figure 2B:
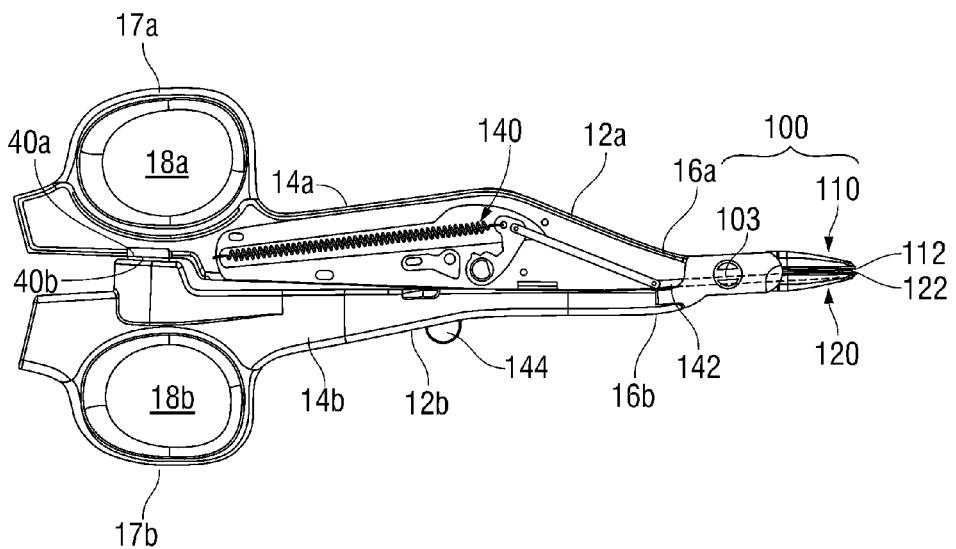
FIG. 2B is a side view of the forceps of FIG. 1 wherein a portion of one of the shaft members has been removed to shown the internal components thereof and wherein the knife assembly is disposed in an extended position.

Referring now to FIGS. 2A-2B, in conjunction with FIG. 1, forceps 10 may further include a knife assembly 140 disposed within one of the shaft members, e.g., shaft member 12a and a knife channel 115, 125 (FIG. 4) defined within one or both of jaw members 110, 120, respectively, to permit reciprocation of knife 142 therethrough. Knife assembly 140 includes a rotatable trigger 144 coupled thereto that is rotatable about a pivot for advancing knife 142 from a retracted position within shaft member 12a (FIG. 2A), to an extended position (FIG. 2B), wherein knife 144 extends into knife channels 115, 125 to divide tissue grasped between jaw members 110, 120. In other words, axial rotation of trigger 144 effects longitudinal translation of knife 142. Other trigger assemblies are also contemplated.

Figure 3:
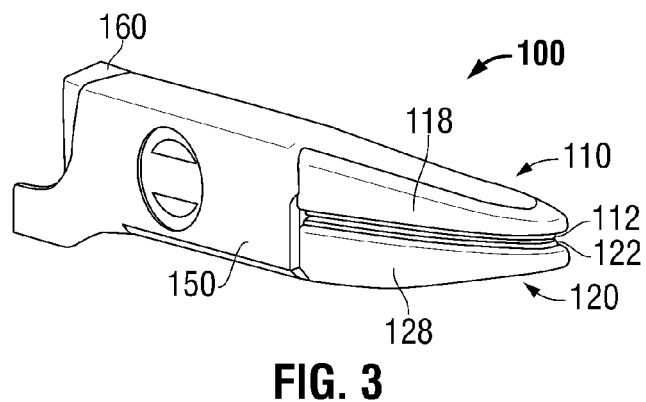
FIG. 3 is a enlarged, perspective view of an end effector assembly configured for use with the forceps of FIG. 1.
Figure 4:
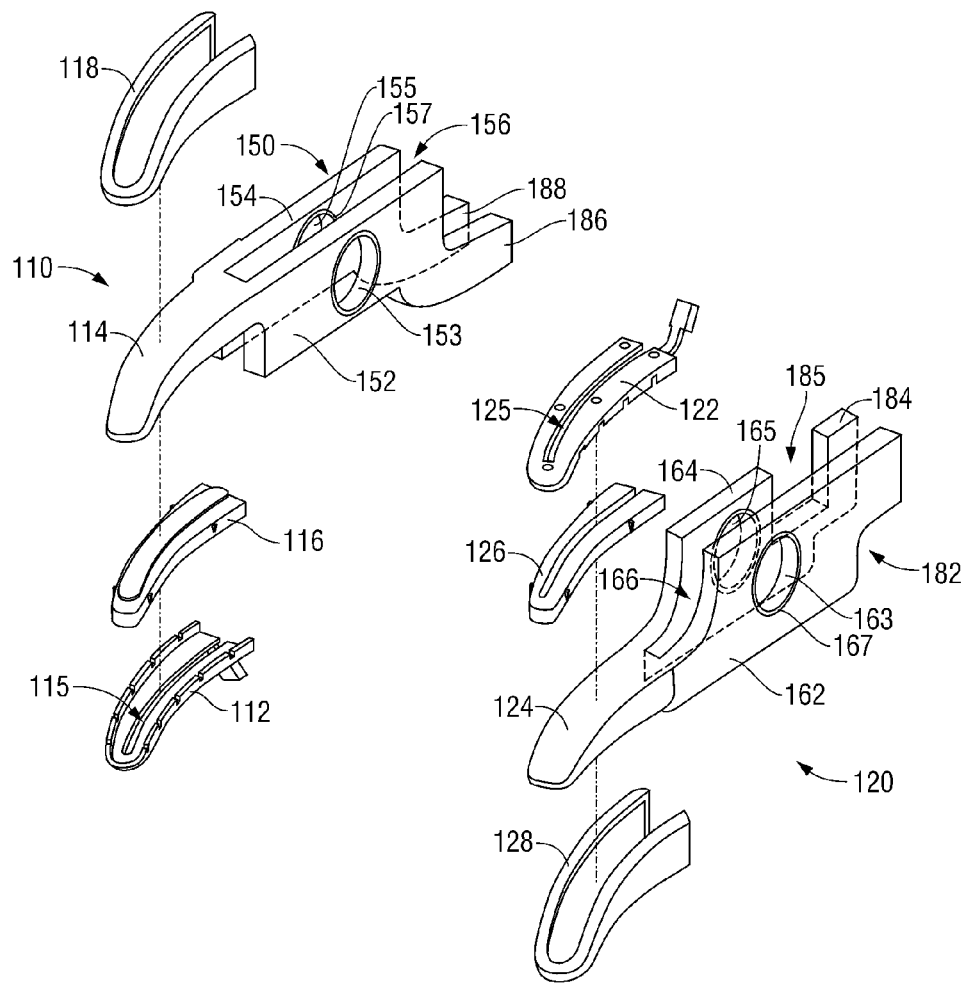
FIG. 4 is a perspective view of the end effector assembly of FIG. 3, shown with parts separated.

Turning now to FIGS. 3-4, each jaw member 110, 120 of end effector assembly 100 includes a jaw frame 114, 124 having a proximal flange 150, 160 extending proximally therefrom. Jaw frames 114, 124 and proximal flanges 150, 160, respectively, thereof may be monolithically formed. In particular, jaw frames 114, 124 may be formed from a plurality of individual layers that are joined together, as will be described in greater detail below. Proximal flanges 150, 160 are engagable with one another to permit pivoting of jaw members 110, 120 relative to one another between the open position and the closed position upon movement of shaft members 12a, 12b (FIG. 1) relative to one another between the spaced-apart and approximated positions. Proximal flanges 150, 160 of jaw members 110, 120 also connect jaw members 110, 120 to the respective shaft members 12b, 12a thereof, e.g., via welding.

Jaw members 110, 120 each further include an insulator 116, 126 disposed atop jaw frames 114, 124, respectively. Insulators 116, 126, in turn, are configured to receive electrically-conductive tissue sealing plates 112, 122, respectively, thereon and are configured to electrically isolate tissue sealing plates 112, 122 from the remaining components of the respective jaw member 110, 120. Outer jaw housings 118, 128 are disposed about tissue sealing plates 112, 122, jaw frames 114, 124, and insulators 116, 126, respectively, and are configured to house these components at least partially therein. More particularly, outer jaw housings 118, 128 may be over-molded about jaw frames 114, 124, insulators 116, 126 and tissue sealing plates 112, 122, respectively, to engage the components of each respective jaw member 110, 120 to one another, although other manufacturing methods are also contemplated.

In the fully assembled condition, as shown in FIG. 3, tissue sealing plates 112, 122 of jaw members 110, 120 are disposed in opposed relation relative to one another such that, upon movement of jaw members 110, 120 to the closed position, tissue is grasped between tissue sealing plates 112, 122, respectively, thereof. Accordingly, in use, electrosurgical energy may be supplied to one or both of tissue sealing plates 112, 122 and conducted through tissue to seal tissue grasped therebetween and/or knife 142 (FIGS. 2A-2B) may be advanced through knife channels 115, 125 of jaw members 110, 120 to cut tissue grasped therebetween.

Figure 5A:
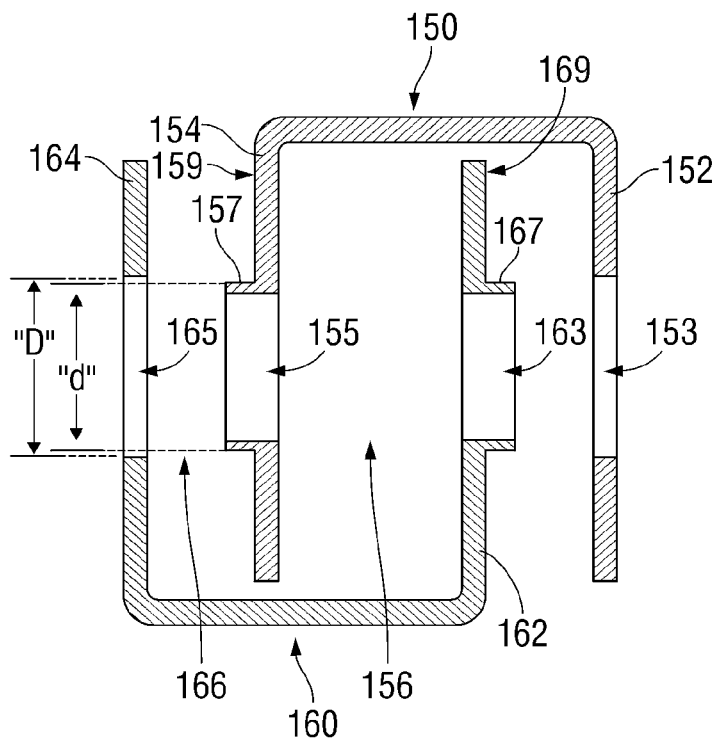
FIG. 5A is a transverse, cross-sectional view of the jaw members of the end effector assembly of FIG. 3 shown in position for assembly.
Figure 5B:
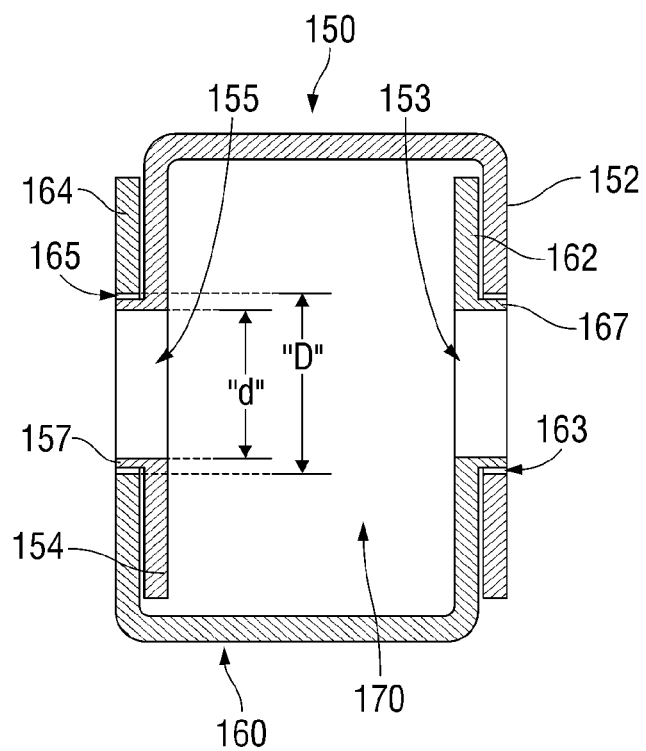
FIG. 5B is a transverse, cross-sectional view of the jaw members of the end effector assembly of FIG. 3 shown engaged to one another.

With continued reference to FIGS. 3-4, in conjunction with FIGS. 5A-5B, proximal flanges 150, 160 of jaw members 110, 120, respectively, each define a generally U-shaped, bifurcated configuration including first and second spaced-apart flange components 152, 154 and 162, 164, respectively. Flange components 152, 154 of proximal flange 150 of jaw member 110 cooperate to define a channel 156 extending longitudinally therebetween that is configured to receive one of the flange components, e.g., flange component 162, of proximal flange 160 of jaw member 120 therein. Flange components 162, 164 of proximal flange 160 of jaw member 120 similarly define a channel 166 extending longitudinally therebetween that is configured to receive one of the flange components, e.g., flange component 154, of proximal flange 150 of jaw member 110 therein. In other words, proximal flanges 150, 160 of jaw members 110, 120, respectively, are configured for positioning relative to one another in an overlapping, offset configuration. However, other configurations, e.g., wherein one of the proximal flanges 150, 160 is completely disposed within the other proximal flange 150, 160, are also contemplated.

Each flange component 152, 154 and 162, 164 of jaw members 110, 120, respectively, includes an aperture 153, 155 and 163, 165, respectively, defined transversely therethrough. Apertures 153, 155 of flange components 152, 154, respectively, of jaw member 110 are aligned with one another and, similarly, apertures 163, 165 of flange components 162, 164, respectively, of jaw member 120 are aligned with one another. Further, each aperture 153, 155, 163, 165 may define a similar diameter "D." One of the flange components of proximal flange 150, e.g., flange component 154, and one of the flange components of proximal flange 160, e.g., flange component 162, each include an annular boss 157, 167, respectively, coaxially disposed adjacent the respective aperture 155, 163 thereof on an outwardly-facing surface 159, 169, respectively, thereof. Annular bosses 157, 167 each define a reduced outer diameter "d" as compared to diameter "D" of apertures 153, 155, 163, 165, i.e., annular bosses 157, 167 extend radially inwardly toward the longitudinal axes of apertures 155, 163, respectively, to cover at least a portion, e.g., the outer periphery, of apertures 155, 163. Due to this configuration, as will be described in greater detail below, when proximal flanges 150, 160 are overlapped with one another, boss 167 of first flange component 162 of jaw member 120 may be pivotably engaged within aperture 153 of first flange component 152 of jaw member 110 and boss 157 of second flange component 154 of jaw member 110 may be pivotably engaged within aperture 165 of second flange component 164 of jaw member 120 in order to pivotable engage proximal flanges 150, 160 and, thus, jaw members 110, 120 to one another.

Continuing with reference to FIGS. 3-4 and 5A-5B, the pivotable coupling of jaw members 110, 120 to one another is described. Initially, jaw member 110 is inverted relative to jaw member 120 such that tissue sealing plates 112, 122 of jaw members 110, 120, respectively, oppose one another. In this position, the U-shaped proximal flanges 150, 160 of jaw members 110, 120, respectively, oppose one another such that each proximal flange 150, 160 may be at least partially inserted into the channel 156, 166 defined within the opposed proximal flange 150, 160, respectively, e.g., to achieve the overlapping, offset configuration of jaw members 110, 120.

With jaw member 110 inverted relative to jaw member 120, proximal flanges 150, 160 are approximated relative to one another such that flange component 154 is disposed within channel 166 of proximal flange 160 of jaw member 120 and such that flange component 162 is disposed within channel 156 of proximal flange 150 of jaw member 110. In other words, in this position, as best shown in FIG. 5A, proximal flanges 150, 160 are disposed in the overlapping, offset configuration wherein annular boss 167 of flange component 162 is positioned adjacent aperture 153 of flange component 152 and wherein annular boss 157 of flange component 154 is positioned adjacent aperture 165 of flange component 164.

In order to pivotably engage proximal flange 150 of jaw member 110 and proximal flange 160 of jaw member 120 to one another, with proximal flanges 150, 160 disposed in the offset, overlapping configuration shown in FIG. 5A, proximal flanges 150, 160 are urged toward one another such that annular boss 167 of flange component 162 is engaged within aperture 153 of flange component 152 and such that annular boss 157 of flange component 154 is engaged within aperture 165 of flange component 164, as shown in FIG. 5B. In this position, flange components 152, 162 are pivotably coupled to one another, i.e., annular boss 167 is rotatably engaged within aperture 153, and are substantially abutting or disposed in close proximity to one another and, similarly, flange components 154, 164 are pivotably coupled to one another, i.e., annular boss 157 is rotatably engaged within aperture 165, and are substantially abutting one another or in close proximity to one another. As such, jaw members 110, 120 may be simultaneously pivoted (e.g., about these two boss-aperture couplings) relative to one another to move jaw members 110, 120 between the open and closed positions for grasping tissue therebetween. Further, this pivotable coupling of bifurcated proximal flanges 150, 160 of jaw members 110, 120, respectively, is advantageous in that channels 156, 166 (collectively, lumen 170) defined within proximal flanges 150, 160, respectively, are substantially uninterrupted. For example, due to this configuration, knife 142 (FIGS. 2A-2B) need not be configured to pass over/under a pivot pin or define a slot therein for receiving the pivot pin therethrough since, instead of a pivot pin extending transversely through lumen 170 (formed by overlapping channels 156, 166 of proximal flanges 150, 160, respectively), proximal flanges 150, 160 are pivotably coupled to one another on either side of lumen 170.

Figure 6A:
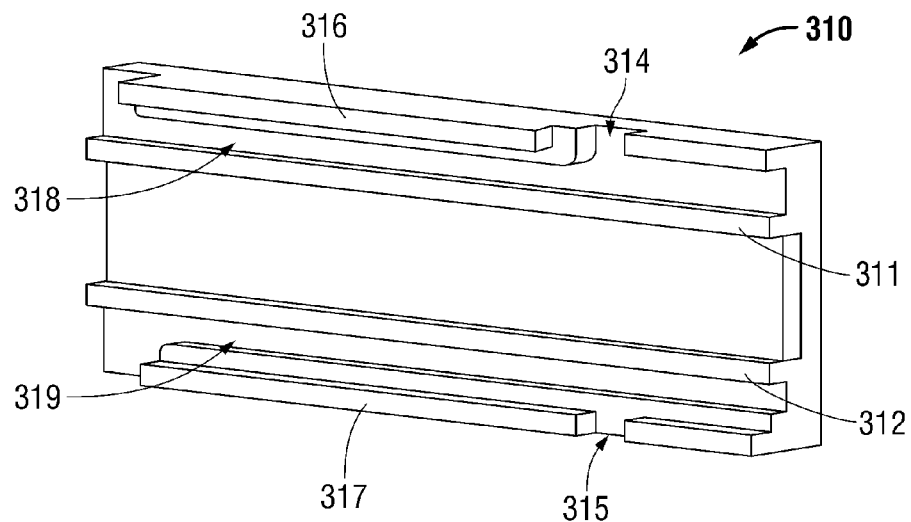
FIG. 6A is a side, perspective view of a first component of a knife guide configured for use with the end effector assembly of FIG. 3.
Figure 6B:
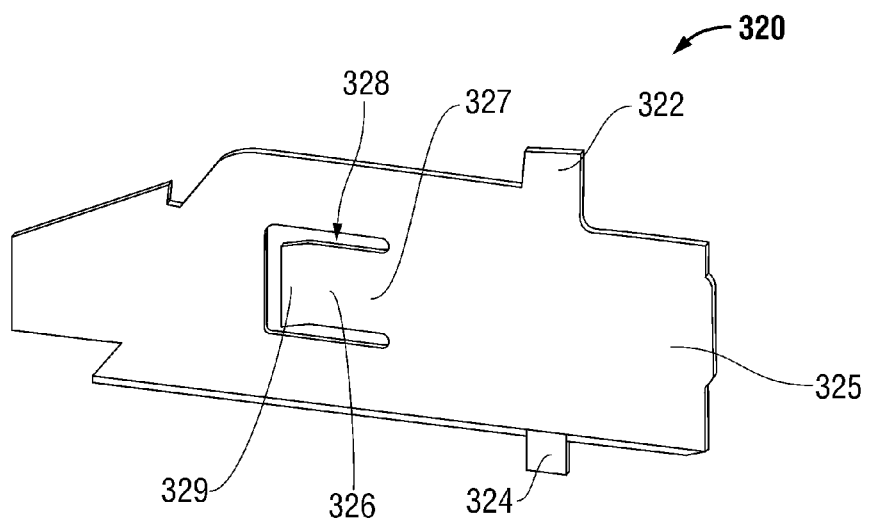
FIG. 6B is a side, perspective view of a second component of the knife guide.
Figure 7:
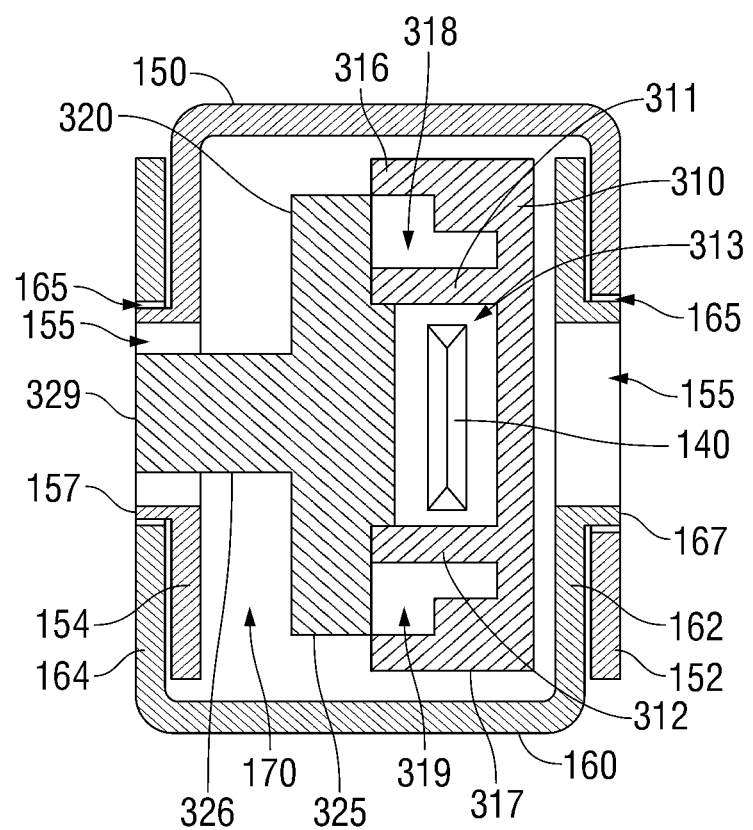
FIG. 7 is a transverse, cross-sectional view of the end effector assembly of FIG. 3 in a fully assembled condition.

Turning now to FIGS. 6A-6B and 7, a guide member formed from first and second guide components 310, 320, respectively, is positionable within lumen 170 formed by proximal flanges 150, 160, respectively, of jaw members 110, 120 for providing support to and for locking proximal flanges 150, 160 in pivotable engagement with one another. Guide components 310, 320 may be formed via stamping, or any other suitable manufacturing process and/or each of guide components 310, 320 may be monolithically formed. As will be described in greater detail below, first and second guide components 310, 320 of the guide member cooperate to guide translation of knife 142 therethrough and into knife channels 115, 125 defined within jaw members 110, 120, respectively, as knife 142 is translated between the retracted and extended positions (see FIGS. 1-4). Guide components 310, 320 are further configured to route and protect the wire(s) (not shown) that extend from cable 210 and through shaft member 12b, ultimately coupling to tissue sealing plate 112 of jaw member 110 and/or tissue sealing plate 122 of jaw member 120 for providing electrosurgical energy thereto for sealing tissue grasped therebetween (see FIGS. 1-4).

Referring to FIGS. 6A and 7, first guide component 310 defines a generally rectangular configuration and is configured for insertion into lumen 170 defined by proximal flanges 150, 160 of jaw members 110, 120, respectively. More specifically, first guide component 310 is configured for longitudinal positioning adjacent one side of lumen 170, e.g., in abutting relation or close proximity relative to proximal flange components 152, 162 of jaw members 110, 120, respectively, such that first guide component 310 extends longitudinally between the components of each of proximal flanges 150, 160. First guide component 310 further includes a pair of longitudinal rails 311, 312 extending longitudinally therealong and protruding transversely therefrom into lumen 170, i.e., in a direction opposite of proximal flange components 152, 162 of jaw members 110, 120, respectively. Rails 311, 312 are spaced apart from one another to define a knife track 313 therebetween that is configured to guide reciprocation of knife 142 therethrough. A pair of opposed slots 314, 315 defined within first guide component 310 outside of, e.g., above and below, rails 311, 312 are configured to engage second guide component 320 (FIG. 6B) therein, as will be described in greater detail below. Further, first and second bars 316, 317 extend longitudinally along and protrude from first guide component 310. Each bar 316, 317 is disposed adjacent to but spaced-apart from one of rails 311, 312, respectively, to define wire guides 318, 319, respectively, therebetween. More specifically, a first wire guide 318 is defined between rail 311 and bar 316, and a second wire guide 319 is defined between rail 312 and bar 317. Wire guides 318, 319 are configured to route and protect the wires (not shown) that extend from electrosurgical cable 210 (FIG. 1) through shaft 12b (FIG. 1) and to tissue sealing plates 112, 122 of jaw members 110, 120, respectively, as mentioned above (see FIG. 4).

With reference now to FIGS. 6B and 7, second guide component 320 similarly defines a generally rectangular configuration and is configured for insertion into lumen 170 defined by proximal flanges 150, 160 of jaw members 110, 120, respectively. More specifically, second guide component 320 is configured for insertion into lumen 170 and for longitudinal positioning adjacent first guide component 310 such that opposed tabs 322, 324 of second guide component 320 are engaged, e.g., via snap-fit engagement, within opposed slots 314, 315 defined within first guide component 310. In this position, body 325 of second guide component 320 abuts longitudinal rails 311, 312 of first guide component 310 to fully enclose knife track 313 defined therebetween. As such, first and second guide components 310, 320 cooperate to define a generally rectangular-shaped cross-sectional knife track 313 that is configured to guide reciprocation of the generally rectangular-shaped knife 142 between the retracted and extended positions and to inhibit splaying of knife 142 as knife 142 is advanced through tissue (see FIGS. 2A-2B). Other knife-track configurations formed complementarily to the knife to be translated therethrough are also contemplated. Body 325 of second guide component 320 also abuts bars 316, 317 when disposed within lumen 170 adjacent first guide component 310 such that wire guides 318, 319 are fully enclosed, thus providing additional protection for the wires (not shown) extending therethrough.

Second guide component 320 further includes a cantilever arm 326 monolithically formed therewith. Cantilever arm 326 extends from fixed end 327 thereof adjacent a window 328 defined within second guide component 320 and includes a free end 329 that is biased outwardly to extend from window 328 and second guide component 320. More specifically, cantilever arm 326 extends from second guide component 320 towards proximal flange components 154, 164 of jaw members 110, 120, respectively. Upon insertion of second guide component 320 into lumen 170 defined by proximal flanges 150, 160 of jaw members 110, 120, respectively, cantilever arm 326 is flexed inwardly into window 328 to permit such insertion. As second guide component 320 is inserted further through lumen 170, free end 329 of cantilever arm 326 is eventually positioned adjacent apertures 155, 165 of flange components 154, 164, of jaw members 110, 120, respectively, thus allowing free end 329 of cantilever arm 326 to return under bias to the extended position, wherein cantilever arm 326 is disposed through apertures 155, 165, i.e., wherein cantilever arm 326 is resiliently biased. This engagement of cantilever arm 326 within apertures 155, 165, retains, or locks proximal flanges 150, 160, of jaw members 110, 120, respectively, in pivotable engagement with one another. Further, first and second guide components 310, 320 may be configured such that, as shown in FIG. 7, first and second guide components 310, 320, substantially occupy the volume of lumen 170, thus providing additional strength and support to jaw members 110, 120 and inhibiting disengagement of proximal flanges 150, 160, splaying of jaw members 110, 120, and/or lateral movement of jaw members 110, 120 relative to one another.

Turning now to FIGS. 1 and 3-4, jaw members 110, 120 of end effector assembly 100 are configured to engage respective shaft members 12b, 12a such that, as mentioned above, movement of shaft members 12a and 12b relative to one another between the spaced-apart position and the approximated position is imparted to jaw members 110, 120 for moving jaw members 110, 120 between the open position and the closed position for grasping tissue therebetween. Jaw members 110, 120 of end effector assembly 100 may be engaged to shaft members 12b, 12a, respectively, via welding, or any other suitable manufacturing process.

Proximal flanges 150, 160 of jaw members 110, 120, respectively, may each include one or more features formed therein to facilitate welding of jaw members 110, 120 to shaft members 12b, 12a, respectively. More specifically, flange component 162 of proximal flange 160 of jaw member 120 may include a cut-out portion 182 configured to mate with a complementary-shaped portion of shaft member 12a to facilitate welding therebetween; flange component 164 of proximal flange 160 of jaw member 120 may include a post 184, spaced-apart from flange component 164 of proximal flange 160 (with slot 185 defined therebetween), that is configured to align with a portion of shaft member 12a to facilitate welding of jaw member 110 and shaft member 12a; and flange components 152, 154 of proximal flange 150 of jaw member 110 may each include a proximally-extending tab 186, 188 configured to provide an attachment area, e.g., a welding area, to facilitate welding jaw member 110 to shaft member 12b. This configuration, wherein each flange component 152, 154 and 162, 164 of jaw members 110, 120, respectively, is welded to the respective shaft member 12b, 12a thereof provides additional strength and support and increased side-to-side rigidity to forceps 10.

Figure 8:
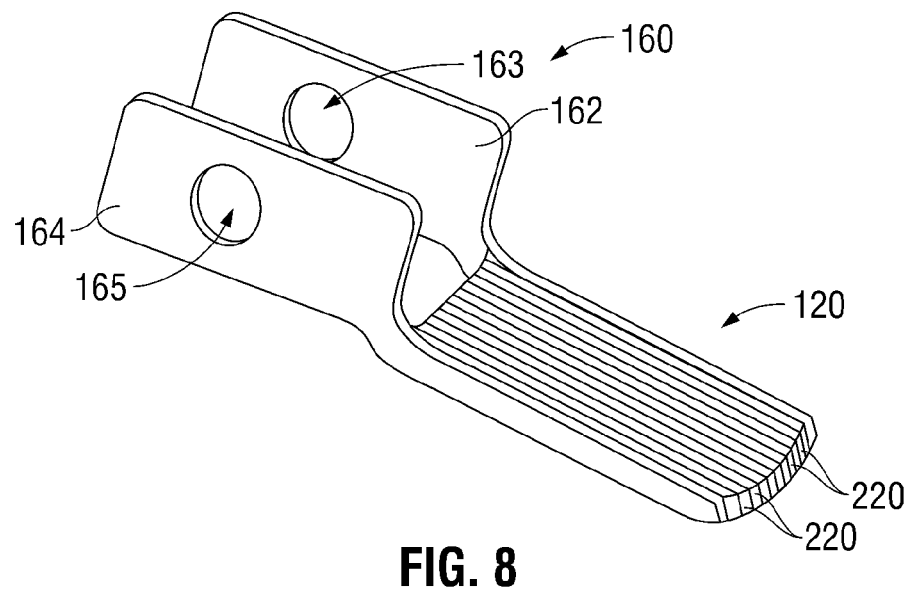
FIG. 8 is a side, perspective view of one of the jaw members of the end effector assembly of FIG. 3.
Figure 9:
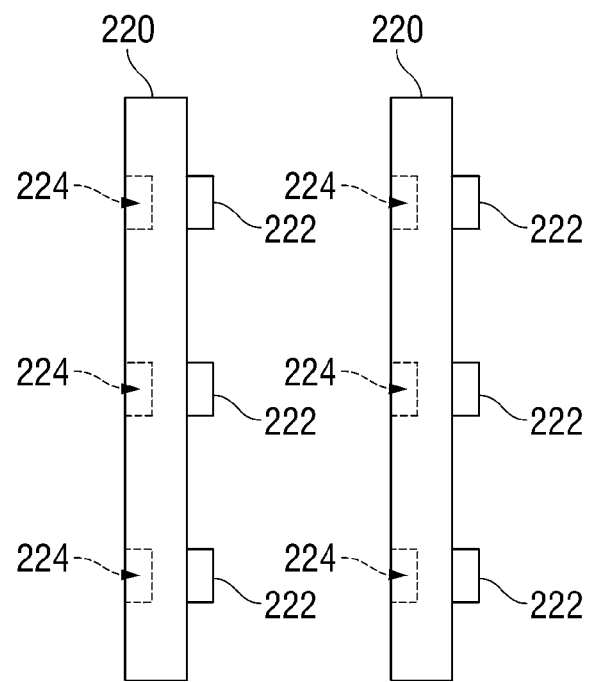
FIG. 9 is a schematic illustration of two of the components used to form the jaw member of FIG. 8.

Referring now to FIGS. 8-9, as mentioned above, jaw members 110, 120 of end effector assembly 100 (see FIG. 4) may each be formed from a plurality of individual layers that are joined together. The manufacture of jaw member 120 will be described in greater detail below. Although only jaw member 120 is shown in FIGS. 8-9 and described below, jaw member 110 may be formed similarly and, thus, will not be described herein for purposes of brevity.

Continuing with reference to FIGS. 8-9, jaw member 120 includes a plurality of individual layers 220 joined together to form the completed jaw member 120. Each layer 220 may be formed from photochemical machining, stamping, or any other suitable manufacturing method. Photochemical machining in particular is advantageous in its ability to machine relatively hard, strong materials that could not be cut by conventional machining techniques. Using a plurality of individual layers 220 as opposed to a single component allows for the use of stronger materials for each layer 220, thus increasing the strength of jaw 120 without requiring an increase in size thereof. Further, this configuration allows any or all of the individual layers 220 to be made from different materials. As such, stronger materials can be used where required, e.g., for those layers 220 forming a portion of proximal flange component 162 or proximal flange component 164, while other materials may be use where added strength is not imperative.

As best shown in FIG. 9, each individual layer 220 may be formed including a plurality of spaced-apart protrusions 222 extending from one side thereof and a plurality of similarly-spaced apertures 224 defined therein on the opposing side thereof. Accordingly, the protrusions 222 of each layer 220 may be engaged within the apertures 224 of the adjacent layer 220 to retain the layers 220 in fixed position, e.g., in the desired configuration, relative to one another. Thereafter, with the layers 220 fixed in the desired configuration, the layers 220 may be joined together, e.g., via integrated forming or welding, to form completed jaw member 120.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An end effector assembly of a surgical instrument, comprising:
    first and second jaw members, each of the jaw members including a proximal flange extending therefrom, each proximal flange defining a bifurcated configuration having first and second spaced-apart flange components, the first flange components of the first and second jaw members configured to pivotably engage one another via a first engagement portion and the second flange components of the first and second jaw members configured to pivotably engage one another via a second engagement portion independent of the first engagement portion, at least one of the first and second jaw members pivotable relative to the other about the first and second engagement portions between an open position and a closed position for grasping tissue therebetween.

2. The end effector assembly according to claim 1, wherein the first flange component of one of the first and second jaw members includes a first aperture defined transversely therethrough, and wherein the first flange component of the other of the first and second jaw members includes a boss, the boss configured for pivotable engagement within the first aperture.

3. The end effector assembly according to claim 2, wherein the second flange component of one of the first and second jaw members includes a second aperture defined transversely therethrough, and wherein the second flange component of the other of the first and second jaw members includes a boss, the boss configured for pivotable engagement within the second aperture.

4. The end effector assembly according to claim 1, wherein the proximal flanges are disposed in an overlapping, offset configuration relative to one another.

5. The end effector assembly according to claim 1, wherein the proximal flanges cooperate to define a lumen extending longitudinally therethrough.

6. The end effector assembly according to claim 1, wherein each of the first and second jaw members defines an opposed electrically-conductive tissue sealing surface, at least one of the electrically-conductive tissue sealing surfaces adapted to connect to a source of energy for treating tissue grasped between the first and second jaw members.

7. A forceps, comprising:
    at least one shaft member;
    an end effector assembly disposed at a distal end of the at least one shaft member, the end effector assembly including:
        first and second jaw members, each of the jaw members including a proximal flange extending therefrom, each proximal flange defining a bifurcated configuration having first and second spaced-apart flange components, the first flange components of the jaw members configured to pivotably engage one another via a first engagement portion and the second flange components of the jaw members configured to pivotably engage one another via a second engagement portion independent of the first engagement portion, at least one of the first and second jaw members pivotable relative to the other about the first and second engagement portions between an open position and a closed position for grasping tissue therebetween.

8. The forceps according to claim 7, further including first and second shaft members, each of the first and second shaft members having one of the first and second jaw members disposed at a distal end thereof such that movement of the first and second shaft members relative to one another between a spaced-apart position and an approximated position effects movement of the first and second jaw members between an open position and a closed position for grasping tissue therebetween.

9. The forceps according to claim 7, further including a knife assembly disposed within the at least one shaft member, the knife assembly including a knife selectively translatable between a retracted position, wherein the knife is disposed within the at least one shaft member, and an extended position, wherein the knife is advanced between the first and second jaw members to cut tissue grasped therebetween.

10. The forceps according to claim 9, wherein the knife is configured to translate through a lumen defined between the proximal flanges.

11. The forceps according to claim 7, wherein the first flange component of one of the first and second jaw members includes a first aperture defined transversely therethrough, and wherein the first flange component of the other of the first and second jaw members includes a boss, the boss configured for pivotable engagement within the first aperture.

12. The forceps according to claim 11, wherein the second flange component of one of the first and second jaw members includes a second aperture defined transversely therethrough, and wherein the second flange component of the other of the first and second jaw members includes a boss, the boss configured for pivotable engagement within the second aperture.

13. The end effector assembly according to claim 7, wherein the proximal flanges are disposed in an overlapping, offset configuration relative to one another.

14. The forceps according to claim 7, wherein each of the first and second jaw members defines an opposed electrically-conductive tissue sealing surface, at least one of the electrically-conductive tissue sealing surfaces adapted to connect to a source of energy for treating tissue grasped between the first and second jaw members.

* * * * *